United States Patent
Rosenbloom

(12) 
(10) Patent No.: US 6,592,896 B2
(45) Date of Patent: Jul. 15, 2003

(54) MEDICINAL COMPOSITION AND METHOD OF USING IT

(75) Inventor: Richard Allen Rosenbloom, Elkins Park, PA (US)

(73) Assignee: The Quigley Corporation, Doylestown, PA (US)

( * ) Notice: Subject to any disclaimer, the term of this patent is extended or adjusted under 35 U.S.C. 154(b) by 0 days.

(21) Appl. No.: 09/923,090

(22) Filed: Aug. 6, 2001

(65) Prior Publication Data

US 2003/0031737 A1 Feb. 13, 2003

(51) Int. Cl.$^7$ .............................. A61K 9/14; A61K 9/20; A61K 35/78
(52) U.S. Cl. ...................... 424/464; 424/439; 424/441; 424/489; 424/756
(58) Field of Search ................................ 424/451, 464, 424/440, 489, 455, 441, 439, 756

(56) References Cited

U.S. PATENT DOCUMENTS

| | | |
|---|---|---|
| 5,120,538 A | 6/1992 | Oei |
| 5,248,504 A | 9/1993 | Friedman |
| 5,385,734 A | 1/1995 | Friedman |
| 5,401,504 A | 3/1995 | Das et al. |
| 5,494,668 A | 2/1996 | Patwardhan |
| 5,707,630 A | 1/1998 | Morrow |
| 5,861,415 A | 1/1999 | Majeed et al. |
| 6,174,542 B1 | 1/2001 | Hinton et al. |

OTHER PUBLICATIONS

Internet Page; 1001 Herbs For a Healthy Life; Slippery Elm; Copyright 2000; 1001 Hebs; pp. 1 and 2.

Internet Page; Slippery Elm—MotherNature.com Health Encyclopedia; Copyright 1995–2000; MotherNature.com Inc.; pp. 1 and 2.

Internet page; Slippery Elm—facts and information; Symmetry Products with Slippery Elm; Cold Rx; p. 1 of 1; Printed on Apr. 10, 2001.

Internet Page; Unconventional therapies for cancer: 2. Green tea (CMAJ—Apr. 21, 1998); Canadian Medical Association Journal; pp. 1 to 8.

Internet Page; Alternative Therapies: From American Journal of Health–System Pharmacy; 57(12):1121–112,2000 Kathryn L. Grant, Pharm.D., Assistant Professor College of Pharmacy, Craig D. Schneider, M.D., Fellow, Program in Integrative Medicine College of Medicine, University of Arizona Tucson; Copyright 2000; pp. 1–6.

Internet Page; Alternative Medicine—Horseradish—Herbal Health Products; Copyright 1996; Viable Herbal Solutions; pp. 1 to 3.

Internet Page; Encyclopedia.com; Results for Horse–Radish; pp. 1 and 2; Copyright 2000, Columbia University Press.

Internet Page; National Library of Medicine; PubMed; Cytotoxicity, antioxidant and anti–inflammatory activities of curcumins I–III from *Curcuma longa;* Ramsewak RS, DeWitt DL, Nair MG; Department of Horticulture and National Food Safety and Toxicology Center, Michigan State University, East Lansing 48824, USA; p. 1; Phytomedicine Jul. 2000; 7(4): 303–8.

Internet Page; National Library of Medicine; PubMed; Anti-–Inflammatory studies on *Curcuma long* (turmeric). Arora, RB, Kapoor V, Basu N, Jain AP; p. 1; Indian J Med Res Aug. 1971; 59(8): 1289–95.

Internet Page; National Library of Medicine; PubMed; Bioactive phytochemicals with emphasis on dietary practices Krishnaswamy K, Raghuramulu, N; National Institute of Nutrition (ICMR), Hyderabad; pp. 1 and 2; Indian J Med Res Nov. 1998; 108: 167–81.

Internet Page; National Library of Medicine; PubMed; Evaluation of anti–inflammatory property of curcumin (diferuloyl methane) in patients with postoperative inflammation; Satoskar RR, Shah SJ, Shenoy SG; p. 1 and 2; Int. J. Clin Pharmacol Ther Toxicol Dec. 1986; 24(12):651–4.

Internet Page; National Library of Medicine; PubMed; Ethnobotany and research on medicinal plants in India; Jain SK; National Botanical Research Institute, Lucknow, India; p. 1 and 2; Ciba Found Symp 1994; 185:153–64; discussion 164–8.

Internet Page; Curcuma—Turmeric; Alternative Medicine Foundation HerbMed; Plain English summaries of major research articles from Medline abstracts with hyperlink to original.; pp. 1 to 13; Copyright 1998.

(List continued on next page.)

Primary Examiner—James M. Spear
(74) Attorney, Agent, or Firm—Knoble & Yoshida, LLC

(57) ABSTRACT

A novel composition for treating symptoms such as symptoms of a common cold, a sore throat, congestion, laryngitis, mucous membrane inflammation and sialorrhea is disclosed. The composition includes ingredients to obtainable from turmeric extract, ginger root powder, and horseradish root powder. This composition can be orally administered a patient. The composition may further include ingredients obtainable from slippery elm bark powder and green tea. This composition may further include a pharmaceutically acceptable carrier for oral administration. A method of administering this composition orally to a patient to treat symptoms of a common cold, a sore throat, congestion, laryngitis, mucositis, sialorrhea and mucous membrane inflammation is also disclosed. To treat these symptoms, the composition is administered to a patient suffering one to fifteen times daily, as needed. To achieve the best effect, the composition should be held in the mouth of a patient for 5 to 60 minutes.

14 Claims, No Drawings

OTHER PUBLICATIONS

Internet Page; Agriculture Research Service; Dr. Duke's Phytochemical and Ethnobotanical Databases; Chemicals and their Biological Activities in: *Curcuma longa* L. (Zingiberaceae)—Indian Saffron, Turmeric; pp. 1 to 19; Printed on Feb. 27, 2001.

Internet Page; Agriculture Research Service; Dr. Duke's Phytochemical and Teehnobotanical Databases; Chemicals and their Biological Activities in: *Armoracia rusticana* Gaertn. et al. (Brassicaceae)—Horseradish; pp. 1 to 17; Printed on Feb. 27, 2001.

Internet Page; Agriculture Research Service; Dr. Duke's Phythochemical and Ethnobotanical Databases; Chemicals and their Biological Activies in: *Ulmus rubra* MUHLENB. (Ulmaceae)—Red Elm, Slippery Elm; pp. 1 to 9; Printed on Feb. 27, 2001.

Internet Page; National Library of Medicine; PubMed; Mechanism of analgesic effect of clonidine in the treatment of dydmenorrhea; Backon J; Mount Pleasant Hospital Addiction Studies Foundation, Lynn, MA; pp. 1 to 2; Med Hypotheses Nov., 1991; 36(3):223–4.

Internet Page; National Library of Medicine; PubMed; Ginger (Zingiber officinale) in rheumatism and musculoskeletal disorders Srivastava KS, Mustafa T; Department of Environmental Medicine, Odense University , Denmark; pp. 1 to 2; Med Hypotheses Dec. 1992; 39(4): 342–8.

Internet Page; Alternative Medicine Foundation HerbMed; Zingiber—Ginger; Plain Enlish summaries of major research articles from Medline abstracts with hyperlink to original; pp. 1 to 12; Copyright 1998 Alternative Medicine Foundation.

Internet Page; Agricultural Research Service; Dr. Duke's Phytochemical and Ethnobotanical Databases; ASCORBIC–ACID; pp. 1 to 4; Printed on Feb. 27, 2001.

Internet Page; Agricultural Research Service; Dr. Duke's Phytochemical and Ethnobotanical Databases; GENTISIC–ACID; pp. 1 to 2; Printed on Feb. 27, 2001.

Internet Page; Agriculture Research Service; Dr. Duke's Phytochemical and Ethnobotanical Databases; Kaemprferol; pp. 1 to 3; Printed on Feb. 27, 2001.

Internet Page; Agriculture Research Service; Dr. Duke's Phytochemical and Ethnobotanical Databases; Chemicals and their Biological Activities in: Zingiber officinate ROSCOE (Zingiberaceae)—Ginger; pp. 1 to 43; Printed on Feb. 27, 2001.

Internet Page; Agriculture Research Service; Dr. Duke's Phytochemical and Ethnobotanical Databases; Biological Activities of ASCORBYL–PALMITATE; p. 1; Printed on Feb. 27, 2001.-

MEDICINAL COMPOSITION AND METHOD OF USING IT

BACKGROUND OF THE INVENTION

A. Field of the Invention

The present invention relates to a medicinal composition and method of using it.

B. Description of the Prior Art

Treatment of Inflammation

In modern non-herbal medicine, there are two major categories of anti-inflammatory medicines: steroidal and non-steroidal. Steroidal anti-inflammatory medicines are powerful medications, which are based on hormonal substances, such as cortisone. These medications have a stronger anti-inflammatory response than the non-steroidal medicines. They can be taken as pills, injected into the bloodstream, or injected directly into a joint space. There are many non-steroidal anti-inflammatory medications. Acetaminophen, aspirin, ibuprofen, and naproxen are the most common ones.

There are side effects to both of these groups of medicines. They include stomach upset, stomach bleeding or ulcers, kidney problems, hearing problems and ankle swelling. Additionally, the steroidal anti-inflammatory medications can have more serious side effects including: loss of bone mass, cataracts, reduced ability to fight infection, swelling and weight gain, mood changes, high blood pressure, and problems with the bone marrow where blood cells are produced.

Treatment of Sialorrhea

Sialorrhea, a symptom related to amyotrophic lateral sclerosis (ALS), is the excessive drooling due to overproduction of saliva from the salivary glands. People have made much effort to treat Sialorrhea. Newall et al reported using beta antagonists to control the excessive secretions of the oral salivary glands and achieve 75% success rates (J. Neurol. Sci., 1996, 139, 43–4). Mier et al have found that ingestion of glycopyrrolate is effective in treating sialorrhea in children. However, 20% of the children being treated with glycopyrrolate experienced substantial adverse effects, enough to require discontinuation of medication (Arch. Pediatr. Adolesc. Med., 2000, 154, 1214–1218).

According to a recent study by Rettori et al. (Ann. N.Y. Acad. Sci., 2000; 917; 258–67), inhibitors of nitric oxide synthase (NOS) decrease stimulated salivary secretions whereas donors of NOS potentiate stimulated salivary secretions. This indicates that nitric oxide exerts a stimulatory role on salivary secretion.

Turmeric (*Curcuma longa*)

Turmeric or Haldi in Hindi is used very widely as medicine as well as a common ingredient in Indian cooking. The rhizome of turmeric is used in medicine and food as a fine powder.

The anti-inflammatory effects of curcumin isolated from *Curcuma longa* were reported in Srimal and Dhawan, Pharmacology of Diferuloyl Methane, a Non-steroidal Anti-inflammatory Agent, J. Pharm. Pharmac. 25:447–452 (1973). Significant anti-inflammatory activity comparable with phenylbutazone and hydrocortisone was observed by Arora et al. (Indian Journal of Medical Research 1971, 59, 1289–1291). Curcumin, an alkaloid (diferuloyl methane) isolated from the alcoholic extract of turmeric has been shown to be a potent anti-inflammatory agent and is considered to be its active ingredient. Further work on anti-inflammatory and anti-arthritic activity has also been carried out by Thatte et al (Indian Journal of Pharmacology 1986, 18 (1), 19–21). Turmeric has been found to have significant anti-inflammatory activity both in acute and chronic models. The therapeutic dose for optimal activity if used alone is reported to be in the range of 5 to 10 grams of dry powder daily (Patwardhan, U.S. Pat. No. 5,494,668). This dosage level, however, can produce a feeling of nausea.

Curcumin not only has anti-inflammatory properties but also has anti-oxidant, anti-tumor and other valuable properties. When used in low concentrations, curcumin can inhibit nitric oxide synthase (NOS) and, therefore, inhibit nitric oxide production. For example, Brouet et al. (Biochem. Biophys. Res. Commun., Jan. 17, 1995; 206 (2); 533–40) have reported that NOS activity in soluble extracts of macrophages activated for 6–24 hours in the presence of curcumin (10 microM) was significantly lower than that of macrophages activated without curcumin. Northern-blot and immunoblotting analyses demonstrated that significantly reduced levels of the mRNA and 130-k Da protein of inducible NOS were expressed in macrophages activated with curcumin, compared to those with curcumin. Inhibition of NOS induction was maximal when curcumin was added together with lipopolysaccharide (LPS) and interferon-gamma (IFN-gamma) and decreased progressively as the interval between curcumin and LPS/IFN-gamma was increased to 18 hours. Therefore, curcumin, when used in an effective amount, may be used to effectively control overproduction of saliva by virtue of its property of acting as a NOS inhibitor.

Ginger (*Zingiber officinale*)

Native to southern Asia, ginger is a 2- to 4-foot perennial that produces grass-like leaves up to a foot long and almost an inch wide. Ginger root, as it is called in the grocery store, actually consists of the underground stem of the plant, with its bark-like outer covering scraped off.

Chinese medical texts from the fourth century B.C. suggest that ginger is effective in treating nausea, diarrhea, stomachaches, cholera, toothaches, bleeding, and rheumatism. Ginger was later used by Chinese herbalists to treat a variety of respiratory conditions, including coughs and the early stages of colds.

Ginger's modern use dates back to the early 1880s, when a scientist named D. Mowrey noticed that ginger-filled capsules reduced his nausea during an episode of flu. Inspired by this, he performed the first double-blind study of ginger. Germany's Commission E subsequently approved ginger as a treatment for indigestion and motion sickness. Ginger has become widely accepted as a treatment for nausea. Even some conventional medical texts suggest ginger for the treatment of the nausea and vomiting of pregnancy, although others are more cautious.

Ginger gives relief from muscular discomfort and pain. It inhibits prostaglandin and leukotriene biosynthesis and histamine release. Thus it acts as an anti-inflammatory as well as an antacid agent. It is a dual inhibitor of the lipoxigenase and cycloxigenase system. Ginger contains 1–4% essential oil (oleoresin). Used alone fresh Ginger is required to be used in substantially high doses (50 grams daily), which is not only inconvenient but can act as an irritant to the gastric mucosa. In dry form for any significant results 7 to 10 grams of dry ginger powder has to be taken daily. These therapeutic doses of ginger are extremely inconvenient for the patient and affect patient compliance on a daily basis. (See Potwardhan, U.S. Pat. No. 5,494,668.)

Horseradish (*Armoracia rusticana*)

Horseradish, a perennial herb (*Armoracia rusticana*, but sometimes classified in other genera) of the family Cruciferae (mustard family), is native to Central and Southern Europe (where it has long been cultivated in gardens) and naturalized in many parts of North America. It is grown mainly for its roots, which formerly were used medicinally, particularly as an antiscorbutic. Horseradish is also an excellent diuretic, and is good for digestion problems. Herbalists combine horseradish and honey for coughs and asthma treatments. Externally, it is sometimes used to alleviate the pain and stiffness caused by rheumatism.

Friedman, U.S. Pat. No. 5,248,504 and U.S. Pat. No. 5,385,734, has used horseradish to treat nasal and sinus dysfunction. Attempts have also been made to provide oral horseradish remedies for certain ailments. Mays, U.S. Pat. No. 98,875, relates to a medical compound for alleviating and curing asthma, coughs and colds. The compound includes pulverized horseradish. Diets, U.S. Pat. No. 74,205, discloses a medical compound containing horseradish for the cure of consumption.

Slippery Elm (*Ulmus rubra*)

Slippery elm trees are native to North American. Slippery Elm has been employed in traditional herbal medicine for over 100 years. The dried inner portion of the slippery elm bark has been used both by Native Americans and early settlers. Slippery Elm is a nutritious food that was made into a type of pudding for those who had weak stomachs. Slippery Elm is soothing to irritated tissues and has been used in poultices for its ability to encourage healing in wounds. Slippery Elm nourishes the adrenal glands, gastrointestinal tract, and respiratory system. It helps the body expel excess mucus. Other conditions, for which slippery elm is used, include: abscess, broken bones, burns and scalds, cholera, colitis, constipation in children, debility, diaper rash, diarrhea in children, diverticulitis, dysentery, hemorrhoids, hiatal hernia, indigestion, labor pain, leprosy and sore throat.

Green Tea (*Camellia sinensis*)

Green tea is the dried leaves and leaf buds of the shrub Camellia Sinensis. It is mainly produced in China and Japan. Dried tea leaves are composed mainly of phytochemcial known as polyphenols (36%), principally flavonols (including catechins), flavonoids and flavondiol. The leaves also contain plant alkaloids (about 4%), including caffeine, theobromine and theophylline. Much of the research on green tea has been focused on its potential to prevent cancer. Research suggests that the polyphenols in green tea are responsible for its chemopreventive effect (E. Kaegi, Canadian Medical Association Journal, 1998, 158: 1033–35).

It is an object of certain embodiments of the present invention to provide a composition, which has a strong anti-inflammatory effect while avoiding or reducing the adverse side effects of some of the foregoing anti-inflammatory medications such as nausea and gastric mucosa irritation.

It is another object of certain embodiments of the present invention to provide a composition for treating some common types of inflammations such as a sore throat, congestion, laryngitis and mucous membrane inflammation.

It is a further object of certain embodiments of the present invention to provide a composition for treating sialorrhea.

It is still a further object of certain embodiments of the present invention to provide a method to treat a sore throat, congestion, laryngitis and mucous membrane inflammation by administering a composition made from natural herbs.

It is still a further object of certain embodiments of the present invention to provide a method to treat sialorrhea by administering a composition made from natural herbs.

These and other objects of the present invention will be apparent from the summary and detailed description of the invention, which follow.

SUMMARY OF THE INVENTION

In a first aspect, the present invention relates to a composition for treating one or more of a common cold, and/or one or more symptoms thereof, a sore throat, congestion, laryngitis, mucositis, mucous membrane inflammation and sialorrhea. The composition includes ingredients which can be obtained from turmeric, ginger and horseradish. It has been found that the combination of these active ingredients provides substantial relief of one or more of these symptoms or ailments.

In a second aspect, the present invention relates to a method to treat one or more of a common cold, and/or one or more symptoms thereof, a sore throat, congestion, laryngitis, mucositis, mucous membrane inflammation and sialorrhea by orally administering to a patient an effective amount of a composition including ingredients which can be obtained from turmeric, ginger and horseradish, which provides substantial relief from one or more of these symptoms.

DETAILED DESCRIPTION OF THE PREFERRED EMBODIMENTS

In a first aspect, the present invention relates to a composition for treating one or more of a common cold, and/or one or more symptoms thereof, a sore throat, congestion, laryngitis, mucositis, mucous membrane inflammation and sialorrhea. The composition includes an ingredient which can be obtained from turmeric, an ingredient which can be obtained from ginger and an ingredient which can be obtained from horseradish. A novel feature of the present invention is the inclusion of these three ingredients together in one composition.

Each of turmeric, ginger, or horseradish contain active ingredients which may provide some beneficial effect in treating one or more symptoms including symptoms of a common cold, a sore throat, congestion, laryngitis, mucositis and mucous membrane inflammation. However, the taste of each of turmeric, ginger, or horseradish at an effective dosage level may be too overpowering for a patient. It has been found that the combination of materials which can be obtained from turmeric, ginger and horseradish in the composition of the present invention provides a substantial beneficial effect, as well as favorable taste characteristics which make the composition palatable.

The first ingredient of the composition of the present invention may be obtained from turmeric. The yellow pigment of the rhizome of turmeric is composed of three compounds known as curcuminoids. The three curcuminoids are curcumin (diferuloylmethane), desmethoxycurcumin (hydroxycinnamoyl feruloylmethane), and bis-desmethoxycurcumin (dihydroxydicinnamoyl methane) (see Drug Analysis by Chromatography and Microscopy, p. 169, Ann Arbor Science Inc., 1973). The essential oils of turmeric (curcuma longa) are primarily composed of the following compounds: d-Camphor (1%), Cyclo-isoprenemyrcene (85%), and p-Tolylmethylcarbinol (5%), (see E. Gunther, The Essential Oil, p. 123–4, Van Nostrand Co., 1955).

The first ingredient, obtained from turmeric, preferably includes curcuminoids, such as curcumin (diferuloylmethane), desmethoxycurcumin (hydroxycinnamoyl feruloylmethane), and bis-desmethoxycurcumin (dihydroxydicinnamoyl methane), and mixtures of two or more of these curcuminoids.

Methods for isolating curcuminoids from turmeric are known, (see Janaki and Bose, An Improved Method for the Isolation of Curcumin From Turmeric, J. Indian Chem. Soc. 44:985 (1967)). Alternatively, curcuminoids for use in the present invention can be prepared by synthetic methods.

The first ingredient which can be obtained from of turmeric can be incorporated into the composition of the present invention in a variety of different forms. Those different forms include extracts of turmeric, one or more the curcuminoid compounds, turmeric powder and mixtures thereof.

The second ingredient of the composition of the present invention may be obtained from ginger (also commonly called ginger root). Non-steroidal anti-inflammatory drugs have three major actions, all of which are related to inhibition of cyclo-oxygenase resulting in decreased formation of prostanoids. Firstly, an anti-inflammatory action achieved by reduced production of vasodilator prostaglandins (PGE2, PGI2), which means less vasodilation and, indirectly less oedema. Secondly, an analgesic effect achieved by reduced prostaglandin production (less sensitization of nociceptic nerve endings to the inflammatory mediators bradykinin and 5-hydroxytryptamine). Thirdly, an antipyretic effect which is probably due to a decrease in the mediator PGE2 generated in response to inflammatory pyrogens, much as interleukin-1. Ginger inhibits prostanoid synthesis and also products of 5-lipoxygenase. The potency of the ginger extract in the acute inflammation test appears to be comparable to that exhibited by acetyl salicylic acid reported in the same study. (Mascolo N. et al Journal of Ethnopharmocology 1989, 27, 129–140).

One of the features of inflammation is increased oxygenation of arachidonic acid, which is metabolized by two enzymic pathways—the cyclooxygenase (CO) and the 5-lipoxygenase (5-LO)-leading to the production of prostaglandins and leukotrienes respectively. It is suggested (Srivastava and Mustafa; Medical Hypotheses; 1992; 39 342–348) that at least one of the mechanisms by which ginger shows its ameliorative effects could be related to inhibition of prostaglandin and leukotriene biosynthesis, i.e. it works as a dual inhibitor of eicosanoid biosynthesis.

Ginger contains 1–4% essential oil (oleoresin). Many chemical investigations have been carried out on the constituents of the essential oil of ginger. All together more than 200 different volatiles have been identified in the essential oil of ginger. The essential oil of ginger contains a mixture of various terpenes as well as some other non-terpenoid compounds.

The active compounds of ginger which may be employed in the present invention include, but are not limited to, 1,8-cineole, 10-dehydrogingerdione, 10-gingerol, 6-gingerdione, 6-gingerol, 6-shogaol, 8-β-17-epoxy-λ-trans-12-ene-15,16-diol, 8-gingerol, 8-shogaol, 9-oxo-nerolidol, acetaldehyde, acetic acid, alanine, α-linolenic-acid, α-linolenic acid, α-phellandrene, α-piene, α-terpinene, α-terpineol, α-zingiberene, ar-curcumene, arginine, ascorbic acid, asparagine, β-bisabolol, β-carotene, β-elemene, β-eudesmol, β-ionone, β-myrcene, β-phellandrene, β-pinene, β-selinene, ,B-sesquiphellandrene, β-sitosterol, β-thujone, bornyl-acetate, boron, caffeic acid, calcium, camphene, camphor, capric acid, caprylic acid, capsaicin, caryophyllene, chavicol, chlorogenic acid, chromium, citral, citronellal, citronellal, cobalt, copper, cumene, curcumin, cystine, delphinidin, δ-cadinene, elemol, ethyl acetate, ethyl-myristate, farnesal, farnesene, ferulic acid, furfural, γ-aminobutyric acid, γ-terpinene, geranial, geraniol, geranyl-acetate, gingerenone, glutamic acid, glycine, hexahydrocurcumin, histidine, isogingerenone-B, isoleucine, kaempferol, lecithin, limonene, linoleic acid, magnesium, manganese, methionine, mufa, myrecene, myricetin, myristic acid, neral, nerol, nerolidol, niacin, nickel, oleic acid, oxalic acid, p-coumaric acid, p-cymene, p-hydroxy-benzoic acid, palmitic acid, pantothenic acid, paradol, patchoulic alcohol, phenylalanine, quercetin, riboflavin, selenium, shikimic-acid, terpinen-4-ol, thiamin, tryptophan, vanillic acid, vanillin, zinc, and zingerone. Also, mixtures of two or more of these active compounds may be employed.

The second ingredient of the composition of the present invention, which may be obtained from ginger, can be incorporated in the composition of the present invention in many different forms including ginger extract, ginger powder, one or more active compounds of ginger and mixtures thereof. Also, for any specific active compound of ginger for which suitable synthesis routes are known, the active compound can be prepared synthetically.

A third ingredient of the composition of the present invention may be obtained from horseradish (also commonly called horseradish root). Horseradish's pharmacological activities are mainly due to its active compounds. The active compounds of horseradish which may be useful in the present invention include, but are not limited to, allyl-isothiocyanate, amylase, arginine, ascorbic acid, asparagine, gentisic acid, kaempferol, limonene, niacin, p-hydroxy-benzoic acid, pectin, phenylpropyl-isothiocyanate, quercetin, raphanin, riboflavin, rutoside, selenium, sinapic acid, sinigrin, tannin, thiamin, vanillic acid and zinc, as well as mixtures of two or more of these compounds.

The third ingredient of the composition of the present invention, which may be obtained from horseradish, can be included in the composition in many different forms. Those different forms include horseradish powder, horseradish extract, one or more active compounds of horseradish and mixtures thereof. For a particular active compound, for which a synthetic route is known, the active compound may be obtained synthetically.

All active compounds of the present invention may be obtained from other sources, if available. Thus, the phrase "which can be obtained from" or the phrase "which may be obtained from" is meant to encompass compounds or compositions that are obtainable from turmeric, ginger, horseradish, slippery elm or green tea and therefore encompasses synthetic forms of the same compounds and/or compositions as well as the same compounds and/or compositions obtained from other sources.

The ingredients of the composition of the present invention, which may be obtained from turmeric, ginger and horseradish, can preferably be used in the forms of turmeric powder, ginger powder, horseradish powder which are ground from the rhizome of turmeric, ginger root and horseradish root respectively. Alternatively, turmeric powder, ginger powder, horseradish powder, and/or one or more of the active compounds contained therein can be purchased from commercial sources such as Delavau Co. Alternatively, the ingredients of the present invention can be used in the form of turmeric extract, ginger extract and horseradish extract, which may be extracted from each of turmeric rhizome, ginger root and horseradish root leaves using common extraction procedures. One suitable extraction procedure is described below.

The extraction procedure comprises, generally, the steps of:
1) cleaning the plant from which the pharmacologically or biologically active plant extract has to be obtained to remove any foreign matter thereon;
2) particulating the plant to obtain a particulate mass having particle size ranging from 0.001 to about 10 mm$^3$; and
3) subjecting the particulate mass to at least one polar and at least one non-polar solvent to obtain separate fractions of the plant extract soluble in the respective solvents, and mixing the fraction so obtained to obtain the beneficiated plant extract in accordance with this invention.

For instance, in the case of turmeric, the process comprises the steps of:
1) cleaning the roots of turmeric to remove any foreign matter thereon;
2) particulating the roots to obtain a particulate mass having particle size ranging from 0.001 to about 10 mm$^3$;
3) subjecting the particulate mass to distillation to obtain a volatile fraction, if any, from the particulate mass;
4) cooking the distilled particulate mass in a polar solvent, such as water to soluble material in the distillation-treated particulate mass to obtain a first solution and a first residue;
5) filtering the first solution from the first residue;
6) evaporating the filtrate obtained from the first solution to remove the solvent and obtain a solute designated as fraction A from the particulated mass;
7) subjecting the first residue to treatment with a second polar solvent such as 75% to 95% ethanol for twelve to thirty-six hours to obtain a second solution and a second residue;
8) filtering the second solution from the second residue to obtain a second filtrate;
9) evaporating the second filtrate to remove its solvent and obtain a solute designated as fraction B from the particulated mass;
10) subjecting the second residue to less polar or non-polar solvents; such as petroleum ether, for twelve to thirty-six hours to obtain a third solution and a third residue, and filtering the third solution from the third residue to obtain a third filtrate;
11) evaporating the third filtrate to remove its solvent and obtain a solute designated as fraction C from the particulated mass; and
12) homogeneously mixing the volatile fraction, with fractions A, B and C from the particulated mass to obtain a beneficiated plant extract.

The process is suitable for the preparation of a pharmacologically or biologically active plant extracts substantially in a convenient administrable dosage form from any of the plants mentioned above.

Solvents useful for extracting turmeric include water, ethanol, propanol, paraffin, hexane, petroleum ether, toluene, acetone, methyl ethyl ketone, and other common organic solvents. Water, ethanol and petroleum ether are the preferred solvents for extracting turmeric. Solvents useful for extracting ginger include water, ethanol, propanol, paraffin, petroleum ether, hexane, toluene, acetone, methyl ethyl ketone, and other common organic solvents. Ethanol, water and acetone are the preferred solvents for extracting ginger. Solvents useful for the extracting horseradish include water, ethanol, propanol, paraffin, petroleum ether, hexane, toluene, acetone, methyl ethyl ketone, and other common organic solvents. Water and ethanol are the preferred solvents for extracting horseradish.

Preferably, the composition of the present invention includes turmeric extract, ginger root powder and horseradish root powder.

Each gram of the composition of the present invention preferably contains 5 mg to 20 mg of turmeric extract. Most preferably, each gram of the composition contains 7 mg to 15 mg of turmeric extract.

Each gram of the composition of the present invention preferably contains 30 mg to 150 mg of ginger root powder. Most preferably, each gram of the composition contains 50 mg to 110 mg of ginger root powder.

Each gram of the composition of the present invention preferably contains 25 mg to 70 mg of horseradish root powder. Most preferably, each gram of the composition contains 40 mg to 60 mg of horseradish root powder.

Preferably, the composition of the present invention may further include a fourth ingredient, namely a suitable demulcent, which may soothe and mobilize mucous membrane in the mouth of a patient. The demulcent may be obtained from slippery elm. Alternatively, the demulcent may be selected from pectin, mucilage and carageenan.

The active compounds of slippery elm which may be useful in the present invention include, but are not limited to, ascorbic acid, β-carotene, β-sitosterol, citrostadienol, magnesium, manganese, mucilage, niacin, riboflavin, selenium, tannin, thiamin, zinc and mixtures thereof.

Preferably, the fourth ingredient of the composition of the present invention, which may be obtained from slippery elm, is incorporated into the composition of the present invention a form selected from slippery elm bark powder, slippery elm extract, one or more active compounds of slippery elm or mixtures thereof. Slippery elm bark powder may be produced by grinding slippery elm bark. Slippery elm extract may be produced by extracting slippery elm bark using well known extraction processes. For a particular active compound, for which a synthetic route is known, the active compound may be synthesized. Alternatively, the slippery elm bark powder, the slippery elm extract and/or the active compounds of slippery elm may be purchased from commercial sources such as Delavau Co.

Preferably, the fourth ingredient of the composition is slippery elm bark powder. Each gram of the composition of the present invention preferably contains 50 mg to 150 mg of slippery elm bark powder. Most preferably, each gram of the composition contains 75 mg to 120 mg of slippery elm bark powder.

Preferably, the composition of the present invention may further include a fifth ingredient which may be obtained from green tea. The fifth ingredient obtained from green tea may have an antioxidant effect.

The pharmacological activities of green tea are mainly due to its active compounds. The active compounds of green tea useful in the present invention include, but are not limited to, flavonols, catechins, flavonoids, flavondiols, plant alkaloids, caffeine, theobromine, theophylline, phenolic acids, proteins, carbohydrates, and minerals.

The fifth ingredient of the composition of the present, which may be obtained from green tea, can be included in the composition in the form of green tea powder, green tea extract, one or more active compounds of green tea or mixtures thereof. The green tea powder can be produced by grinding dry green tea leaves. The green tea extract may be produced by extracting dry green tea leaves using the common extraction methods. For a particular active compound of green tea, for which a synthetic route is known, the active compound may be synthesized. Alternatively, the green tea powder, the green tea extract and/or the active compounds of green tea can be purchased from commercial sources such as Delavau Co.

More preferably, the fifth ingredient of the composition of the present invention, which may be obtained from green tea, is green tea extract. Each gram of the composition of the present invention preferably contains 5 mg to 20 mg of green tea extract. Most preferably, each gram of the composition contains 7 mg to 15 mg of green tea extract.

The composition of the present invention can be used to treat one or more of a common cold and/or one or more symptoms thereof, a sore throat, congestion, laryngitis mucositis, and/or mucous membrane inflammation by oral administration to a patient suffering from one or more of these symptoms or ailments. The composition of the present invention can be also used to treat sialorrhea caused, for example, by ALS.

The compositions of the present invention may be formulated using the three main ingredients discussed above and one or more of the optional ingredients which may be obtained from slippery elm or green tea, as well as one or more of the additional optional ingredients described below. The compositions of the present invention may also be formulated with a pharmaceutically acceptable carrier.

Preferably, the compositions of the present invention may be formulated in any orally acceptable dosage forms including, but not limited to, capsules, tablets, lozenges, troches, hard candies, powders, sprays, elixirs, syrups, and suspensions or solutions.

The pharmaceutically acceptable carrier includes but is not limited to: (a) carbohydrates including fructose, sucrose, sugar, dextrose, starch, lactose, maltose, maltodextrins, corn syrup solids, honey solids, commercial tablet compositions including Emdex.RTM., Mor-Rex.RTM., Royal-T.RTM., Di-Pac.RTM., Sugar-Tab.RTM., Sweet-Rex .RTM., New-Tab.RTM., (b) sugar alcohols including mannitol, sorbitol, xylitol, and (c) various relatively insoluble excipients including dicalcium phosphate, calcium sulfate, calcium carbonate, microcrystalline cellulose and other pharmaceutical tableting ingredients.

Lozenges, tablets and troches in this invention are essentially the same, but may differ in shape, size and manufacturing technique.

In the case of tablets, for oral use, the pharmaceutically acceptable carrier may further include lactose and corn starch. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin, PEG-8000 and gum acacia.

In the case of lozenges for oral use, the common pharmaceutically acceptable carrier may further include a binder such as PEG-8000. Preferably lozenges are made in a 0.1 to 15 grams size to allow a suitable dissolution rate for lozenges. More preferably lozenges are made in an 1 to 6 gram size to allow a suitable dissolution rate for lozenges. Dissolution time should be about 15 minutes in water bath testers at 37° C. degrees or about 30 minutes when orally dissolved as lozenges for treating a sore throat, congestion, laryngitis and mucous membrane inflammation.

To directly make compressible lozenges, add the active ingredients to PEG-8000 processed fructose; or add the active ingredient of the composition to crystalline fructose and commercially available, sweet, direct compression products such as Mendell's Sugartab.RTM., Sweetrex.RTM., or Emdex.RTM. Add saccharin if desired, flavors as desired, glidants such as silica gel as needed, and lubricants such as magnesium stearate as needed. The mixture should be kept dry and tableted soon after mixing. The ingredients are mixed and directly compressed into lozenges using conventional pharmaceutical mixing and tableting equipment. The compressive force is preferably sufficient to produce maximum hardness throughout the lozenges to preserve the dissolution rate and maximize the efficacy of lozenges. Dissolution should occur over a sustained period of time, that being 5 to 60 minutes, and preferably about 20 to 30 minutes. The composition should be stored in an air tight container and in a cool dark place.

Tablets and troches can be manufactured using procedures similar to that described above with minor changes in the optional ingredients.

Alternatively, the composition of the present invention may be formulated in liquid form, such as syrups, mouthwashes or sprays with a solvent or dispersant such as water, or other liquids in a pharmaceutically acceptable carrier for repeated delivery of the composition to oral and oropharyngeal mucous membranes over a sustained period of time. Preferably, the treatment time is about 5 to 60 minutes, and more preferably about 20 to 30 minutes, so as to permit a prolonged contact of the composition with mouth and throat tissues.

The composition may also be formulated in chewable compositions such as soft candy, gum drops, liquid filled candies, chewing gum bases and dental supplies, such as toothpastes and mouthwashes by further including fructose, sucrose, or saccharin in the composition, as needed. In use, the chewable composition is retained in the mouth over a sustained period of time of preferably about 5 to 60 minutes, and more preferably about 20 to 30 minutes.

The composition of the invention may be formulated in capsule form with or without diluents. For capsules, useful diluents include lactose and dried corn starch. When suspensions are employed, emulsifying and/or suspending agents may be employed in the suspensions. In addition, solid compositions including one or more of the ingredients of the lozenges described above may be employed in soft and hard gelatin capsules.

The compositions of the present invention may also be formulated into a nasal aerosol or inhalant. Such compositions may be prepared using well known techniques. For these types of formulations, suitable carriers may include the following ingredients: saline with one or more preservatives, absorption promoters to enhance bioavailability, fluorocarbons and/or other conventional solubilizing or dispersion agents.

Other materials which may optionally be included in the compositions of the present invention include inositol, other B-complex vitamins, and anti-inflammatories. Also, ingredients such as sweeteners, flavorants, coloring agents, dyes, and diluents such as water, ethanol, propylene glycol, glycerin and various combinations thereof, may be included in the compositions of the present invention.

The optional sweeteners which may be used in the compositions of the present invention include, but are not limited to, saccharin, aspartame, cyclamates, acesulfame K, neohesperidin dihydrochalcone, other super sweeteners, and mixtures thereof, which may be added to the carrier in amounts sufficiently low so as not to chemically interact with the main ingredients of the composition.

The optional flavorants which may be used in the compositions of the present invention include, but are not limited to, peppermint, peppermint-menthol, eucalyptol, wintergreen, licorice, clove, cinnamon, spearmint, cherry, lemon, orange, lime, menthol and various combinations thereof.

In general, the three main ingredients described above which may be derived from turmeric, ginger and horseradish, make up from about 0.5–90% by weight of the total composition. Preferably, the three main ingredients will make up 10–70% by weight of the total composition. More preferably, the three main ingredients make up 20–40% by weight of the total composition.

In a second aspect, the present invention relates to a method of administering to a patient an amount of the composition of the present invention, which is effective to provide substantial relief of one or more symptoms of a common cold, as well as one or more of a sore throat, congestion, laryngitis, mucositis, mucous membrane inflammation and sialorrhea.

The method of the present invention involves the administration of a composition of the present invention to a patient that suffers from one or more of a common cold, a sore throat, congestion, laryngitis, mucositis, sialorrhea and mucous membrane inflammation. The effective amount of the composition will vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the composition, and the severity of the illness or symptom. It is within the skill of the person of ordinary skill in the art to account for these factors.

The composition may be administered 1–15 times per day, as needed, more preferably, 2–12 times per day, as needed, or most preferably, 6–10 times per day, as needed. As discussed above, the composition of the present invention may be administered to a patient in any orally acceptable dosage form including, but not limited to tablets, capsules, lozenges, troches, hard candies, powders, sprays, elixirs, syrups, and suspensions or solutions.

The method of the present invention initially treats acute symptoms but may be continued indefinitely to provide substantial relief of one or more, a common cold, a sore throat, congestion, laryngitis, mucositis, sialorrhea, and mucous membrane inflammation, to prevent the symptoms of a common cold, sore throat, congestion, laryngitis and mucous membrane inflammation from returning and possibly cure one or more of these symptoms or ailments.

Preferably, during each administration of the composition, the composition is held in the mouth of the patient for at least 5 to 60 minutes to enable the main ingredients of the composition to contact the mouth tissue or throat before it completely dissolves. More preferably, the composition is held in the mouth of the patient for at least 15 to 30 minutes.

Preferably, an effective amount of the composition for each administration contains 0.1 gram to 1 gram of the three main ingredients which may be obtained from turmeric, ginger and horseradish. More preferably, an effective amount of the composition for each administration contains 0.2 gram to 0.5 gram of the three main ingredients.

For treatment of sialorrhea, significantly less frequent dosages may be sufficient to provide effective relief. Preferably, 1–6 doses per day are used for sialorrhea. More preferably, only 1–2 doses per day are employed to treat sialorrhea.

The invention will be further illustrated by the examples given below which are not to be construed as limiting the invention in any way.

EXAMPLES

Example 1

A Composition of the Present Invention

A composition of the present invention formulated in the form of lozenges was prepared using the procedure described above. The ingredients of the lozenge are listed below:

| | |
|---|---|
| Sugar | 1 g |
| Slippery elm bark | 118 mg |
| Turmeric extract (5% curcumin) | 18 mg |
| Ginger root | 140 mg |
| Horseradish root | 70 mg |
| Green tea leaf extract (30% catechin and polyphenols) | 14 mg |

Example 2

Treatment of Sore Throat

Each of seven patients, suffering from sore throats, ingested one lozenge of Example 1 every two hours by holding the lozenge in his or her mouth for about 15–30 minutes until the lozenge completely dissolves. No patient took more than 10 lozenges in any given day.

The patients, that were treated, reported complete relief from the symptoms of their sore throats after ingesting from 2 to 20 lozenges. It was also found that each lozenge can provide relief from a sore throat for up to 6 hours.

Example 3

Treatment of Sialorrhea

Two patients, who suffer from sialorrhea caused by ALS, ingested 1–2 lozenges of example 1 every day for a three-week period. It was found that the ingestion of the lozenges effectively controlled excessive secretions of saliva in these two patients. In both patients, excessive drooling was also significantly reduced.

Changes may be made in carrying out the methods and to the compositions of the invention above set forth above without departing from the spirit and scope of the invention. It is intended that all matter contained in the above description shall be interpreted as illustrative and not in a limiting sense. The scope of this invention is to be determined from the claims appended hereto.

I claim:

1. A medicinal composition comprising:
   a first ingredient obtainable from turmeric;
   a second ingredient obtainable from ginger; and
   a third ingredient obtainable from horseradish, and wherein the first, second and third ingredients are present in the composition in amounts effective to together provide substantial relief of one or more symptoms selected from the group consisting of symptoms of a common cold, a sore throat, congestion, laryngitis, mucositis, mucous inflammation and sialorrhea.

2. A composition as claimed in claim 1, wherein the first ingredient comprises turmeric extract.

3. A composition as claimed in claim 2, wherein the composition comprises from about 5 mg to about 20 mg of turmeric extract per gram of the composition.

4. A composition as claimed in claim 1, wherein the second ingredient comprises ginger root powder.

5. A composition as claimed in claim 4, wherein the composition comprises from about 30 mg to about 150 mg of ginger root powder per gram of the composition.

6. A composition as claimed in claim 1, wherein the third ingredient comprises horseradish root powder.

7. A composition as claimed in claim 6, wherein the composition comprises from about 25 mg to about 75 mg of horseradish root powder per gram of the composition.

8. A composition as claimed in claim 1, further comprising a fourth ingredient obtainable from slippery elm.

9. A composition as claimed in claim 8, wherein the fourth ingredient comprises slippery elm bark powder and is included in the composition in an amount of from about 50 to about 150 mg per gram of the composition.

10. A composition as claimed in claim 1, further comprising a fifth ingredient obtainable from green tea.

11. A composition as claimed in claim 10, wherein the fifth ingredient comprises green tea extract and is included in the composition in an amount of from about 5 to about 20 mg per gram of the composition.

12. A composition as claimed in claim 1, further comprising a pharmaceutically acceptable carrier.

13. A composition as claimed in claim 1, wherein said composition is formulated into a form selected form the group consisting of lozenges, troches, and tablets.

14. A medicinal composition comprising:
   turmeric extract;
   ginger root powder;
   horseradish root powder;
   slippery elm bark powder;
   a green tee extract; and
   a pharmaceutically acceptable carrier, and wherein the turmeric extract, ginger root powder and horseradish root powder are present in the composition in amounts effective to together provide substantial relief of one or more symptoms selected from the group consisting of symptoms of a common cold, a sore throat, congestion, laryngitis, mucositis, mucous membrane inflammation and sialorrhea.

\* \* \* \* \*